(12) United States Patent
Loke et al.

(10) Patent No.: US 12,324,753 B2
(45) Date of Patent: Jun. 10, 2025

(54) INTERBODY TRIAL INSTRUMENT WITH SCREW TRAJECTORY INDICATORS

(71) Applicant: Warsaw Orthopedic, Inc., Warsaw, IN (US)

(72) Inventors: Robert M. Loke, Memphis, TN (US); Cristian A. Capote, Memphis, TN (US); Stanley Kyle Hayes, Mission Viejo, CA (US); Darren L. Davis, Knoxville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/960,235

(22) Filed: Oct. 5, 2022

(65) Prior Publication Data
US 2024/0115396 A1 Apr. 11, 2024

(51) Int. Cl.
*A61F 2/46* (2006.01)
*A61F 2/44* (2006.01)

(52) U.S. Cl.
CPC .......... *A61F 2/4684* (2013.01); *A61F 2/4455* (2013.01); *A61F 2/4611* (2013.01)

(58) Field of Classification Search
CPC .......... A61F 2/4611; A61F 2/4455–447; A61F 2/4684; A61F 2/44–2022/4495
See application file for complete search history.

(56) References Cited

U.S. PATENT DOCUMENTS

| | | | |
|---|---|---|---|
| 6,113,639 A * | 9/2000 | Ray | A61F 2/4684 623/17.16 |
| 7,300,441 B2 | 11/2007 | Haid et al. | |
| 7,708,780 B2 | 5/2010 | Zubok et al. | |
| 7,942,903 B2 | 5/2011 | Moskowitz et al. | |
| 8,298,235 B2 | 10/2012 | Grinberg et al. | |
| 9,592,129 B2 * | 3/2017 | Slivka | A61F 2/44 |
| 9,622,759 B2 | 4/2017 | Jansen | |
| 11,090,068 B2 | 8/2021 | Giri et al. | |
| 11,273,057 B2 * | 3/2022 | Walsh | A61B 17/8894 |
| 2003/0014113 A1 * | 1/2003 | Ralph | A61B 17/025 623/17.16 |
| 2004/0215198 A1 * | 10/2004 | Marnay | A61B 17/1735 606/86 R |
| 2005/0038511 A1 | 2/2005 | Martz et al. | |
| 2006/0200243 A1 * | 9/2006 | Rothman | A61F 2/4611 623/17.13 |

(Continued)

*Primary Examiner* — Julianna N Harvey
(74) *Attorney, Agent, or Firm* — FOX ROTHSCHILD LLP

(57) ABSTRACT

An orthopedic trialing instrument may include a shaft extending from a first end to a second end, a handle coupled to the shaft, and a first interbody trial disposed on the first end. In various embodiments, the first interbody trial may include a first bone screw indicator configured to visually represent a corresponding bone screw trajectory. In some embodiments, a double-sided orthopedic trialing instrument may include a first interbody trial on a first end and a second interbody trial on a second end. In various embodiments, each of the first interbody trial and second interbody trial may have at least one bone screw protrusion configured to visually represent a corresponding bone screw trajectory. In some embodiments, a plurality of orthopedic trialing instruments having differently sized interbody trials may be provided as a kit.

12 Claims, 8 Drawing Sheets

(56) References Cited

U.S. PATENT DOCUMENTS

| | | | |
|---|---|---|---|
| 2008/0269756 A1* | 10/2008 | Tomko | A61B 17/1757 606/86 R |
| 2009/0177195 A1 | 7/2009 | Rawles et al. | |
| 2016/0030067 A1* | 2/2016 | Frey | A61B 50/33 606/86 A |
| 2019/0105183 A1* | 4/2019 | Adamo | A61F 2/447 |
| 2020/0146697 A1* | 5/2020 | Giri | A61F 2/447 |
| 2021/0085482 A1 | 3/2021 | Flickinger et al. | |
| 2021/0153879 A1* | 5/2021 | Walsh | A61B 17/1631 |
| 2021/0369467 A1 | 12/2021 | Seex | |

* cited by examiner

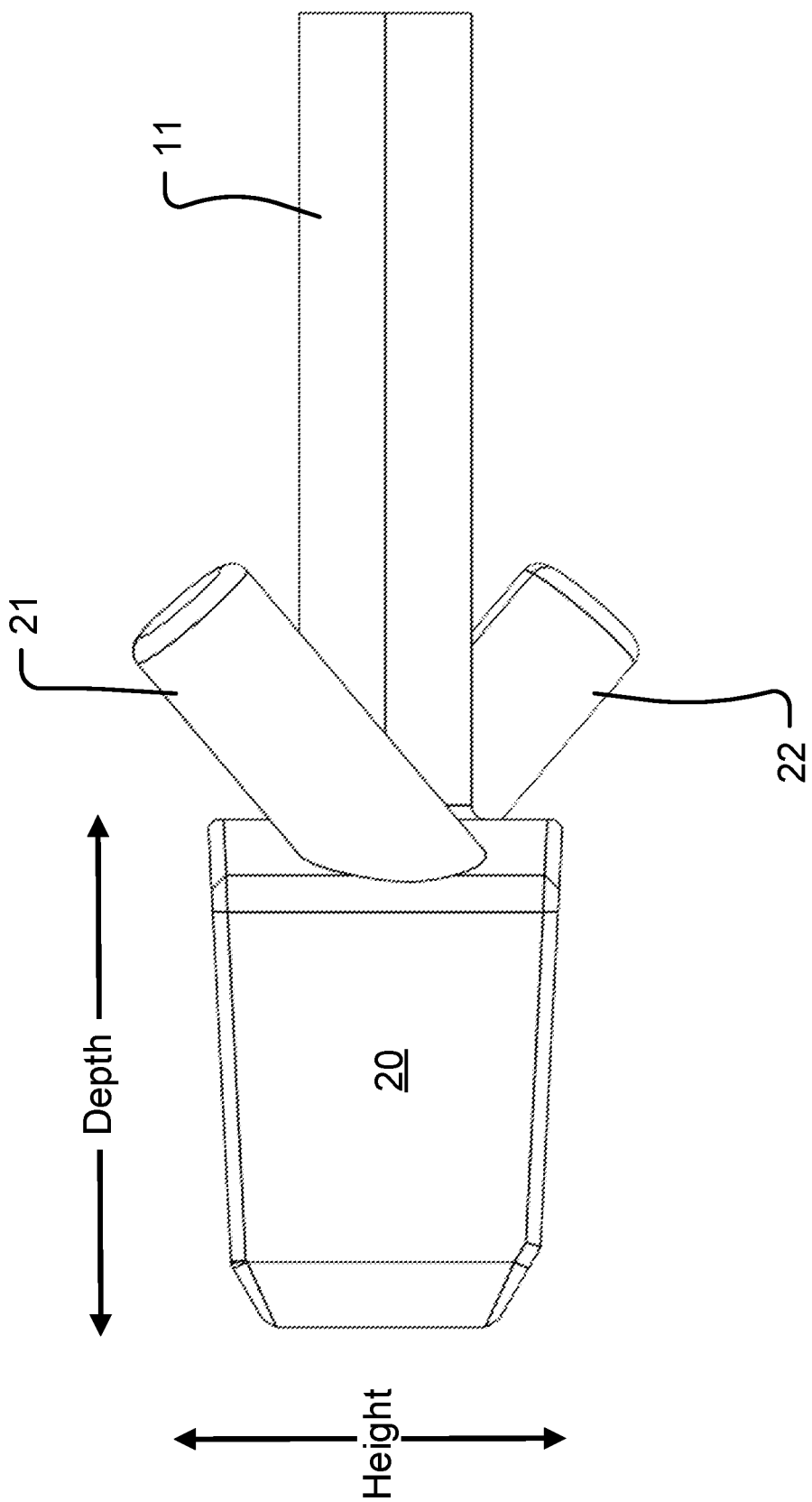

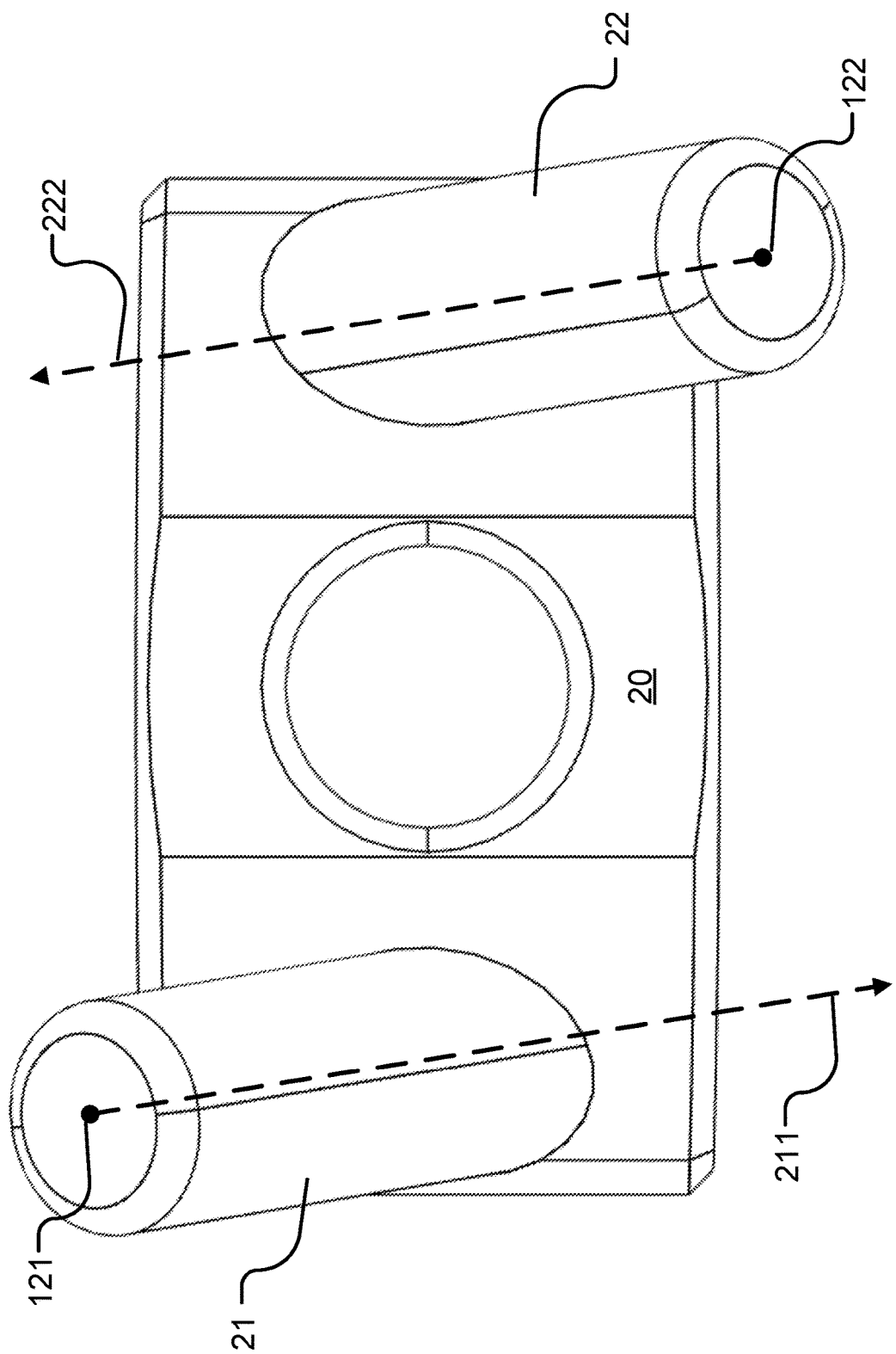

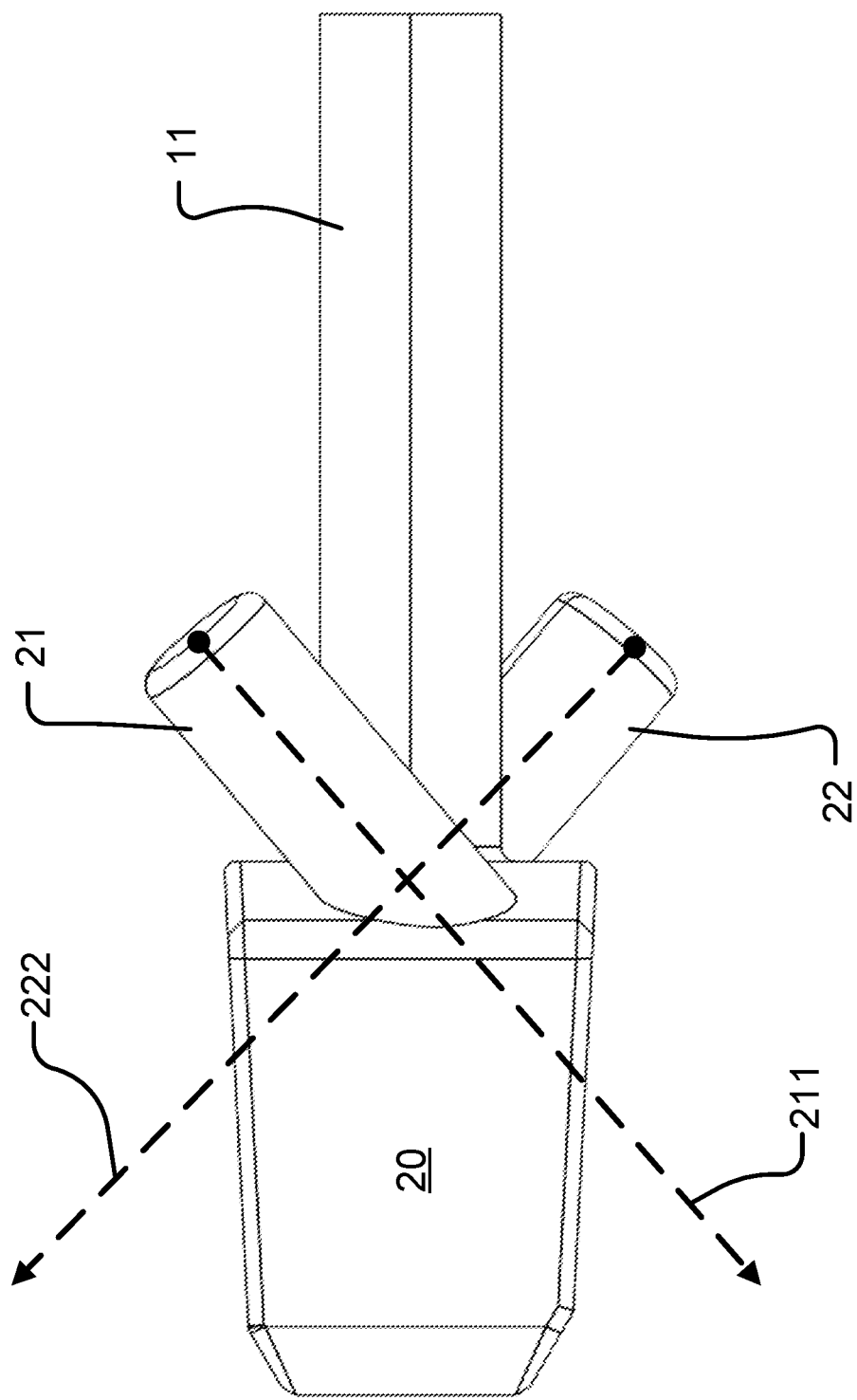

100

200

INTERBODY TRIAL INSTRUMENT WITH SCREW TRAJECTORY INDICATORS

FIELD

The present technology is generally related to instruments for determining an appropriate size, location, and/or orientation of an orthopedic implant to be implanted between adjacent boney structures. Various instruments may include a trial including screw trajectory indicators that serve as physical approximations of a bone screw trajectory for visually identifying an appropriate location or access to the bone for an interbody implant between adjacent vertebra, for example.

BACKGROUND

Interbody implants may be placed between adjacent boney structures in a patient. Some interbody implants may be placed between adjacent vertebra in a human spine, for example. Interbody implants may include an aperture or slot or hole to receive a bone screw that fixes the interbody implant to the adjacent vertebra to stabilize the device between the vertebra until fusion between the vertebra above and below occurs. In at least one method of operation, an interbody implant may be placed into a disc space once the cartilaginous material of the disc is removed and thereafter bone screws may be driven through an aperture or slot or hole of the implant into the adjacent vertebral bodies to stabilize or fixate the device into position. The stabilization or fixation maintains the relative position for the two vertebra to fuse together in order to realign and relieve the pressure off of the nerves exiting from the foramen between the vertebra. Without the use of a trial, in. many instances, it may be difficult for a surgeon to ascertain a suitable size, location, and/or orientation of the interbody implant such that the bone screws will align and clear any boney anatomy that may be in the way along an optimal bone screw trajectory for a specific patient. For example, a surgeon may have difficulty knowing what an appropriate size, location, and/or orientation of an interbody implant may be such that the aperture or slot or hole for supporting the bone screw is positioned optimally such that the bone screw will clear boney anatomy or osteophytes to penetrate into the adjacent vertebral bodies at a desired location such as the cortical rim. This may require the surgeon to remove additional osteophytes or boney anatomy in order to ensure the screws have a clear trajectory for placement. When using trials without screw trajectory indicators, the need to perform additional bone removal is only determined after the interbody is placed, the placement of bone screws is seen to be impeded, and then the interbody is subsequently removed.

SUMMARY

The techniques of this disclosure generally relate to trialing instruments for assisting a surgeon in visualizing a target path and/or trajectory of a bone screw extending through an orthopedic implant. In one aspect, the present disclosure provides an orthopedic trial instrument. In various embodiments, the trial instrument may include a shaft extending from a first end to a second end, a handle coupled to the shaft, and a first interbody trial disposed on the first end. In various embodiments, the first interbody trial may include a first bone screw indicator configured to visually represent a corresponding bone screw trajectory.

In another aspect, the disclosure provides for a double-sided orthopedic trial instrument. The instrument may include a shaft extending in a longitudinal direction from a first end to a second end, a handle disposed at a medial position of the shaft, and a first interbody trial disposed on the first end. In various embodiments, the first interbody trial may include at least one bone screw protrusion configured to visually represent a corresponding bone screw trajectory. In various embodiments, a second interbody trial may be disposed on the second end. In disclosed embodiments, the second interbody trial may include at least one bone screw protrusion configured to visually represent a corresponding bone screw trajectory.

In another aspect, the disclosure provides for an orthopedic trialing instrument kit. In various embodiments, the trialing instrument kit may include a first double-sided orthopedic trial instrument and a second double-sided orthopedic trial instrument. In disclosed embodiments, the first double-sided orthopedic trial instrument may include a first shaft extending in a longitudinal direction from a first end to a second end, a first handle disposed at a medial position of the first shaft, and a first interbody trial disposed on the first end. In disclosed embodiments, the first interbody trial may include a first bone screw indicator configured to visually represent a corresponding bone screw trajectory and a second bone screw indicator configured to visually represent a corresponding bone screw trajectory. In disclosed embodiments, a second interbody trial may be disposed on the second end. The second interbody trial may include a third bone screw indicator configured to visually represent a corresponding bone screw trajectory and a fourth bone screw indicator configured to visually represent a corresponding bone screw trajectory. In disclosed embodiments, the second double-sided orthopedic trial instrument may include a second shaft extending in a longitudinal direction from a third end to a fourth end, a second handle disposed at a medial position of the second shaft, and a third interbody trial disposed on the third end. In disclosed embodiments, the third interbody trial may include a fifth bone screw protrusion configured to visually represent a corresponding bone screw trajectory and a sixth bone screw protrusion configured to visually represent a corresponding bone screw trajectory. In disclosed embodiments, a fourth interbody trial may be disposed on the fourth end. The fourth interbody trial may include a seventh bone screw protrusion configured to visually represent a corresponding bone screw trajectory and an eighth bone screw protrusion configured to visually represent a corresponding bone screw trajectory.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 5 is a front view of the first interbody trial portion of FIG. 4.

FIG. 6 is a right section view of the first interbody trial portion of FIG. 4.

FIG. 7 is a front view of the first interbody trial portion of FIG. 4.

DETAILED DESCRIPTION

Figure 1:
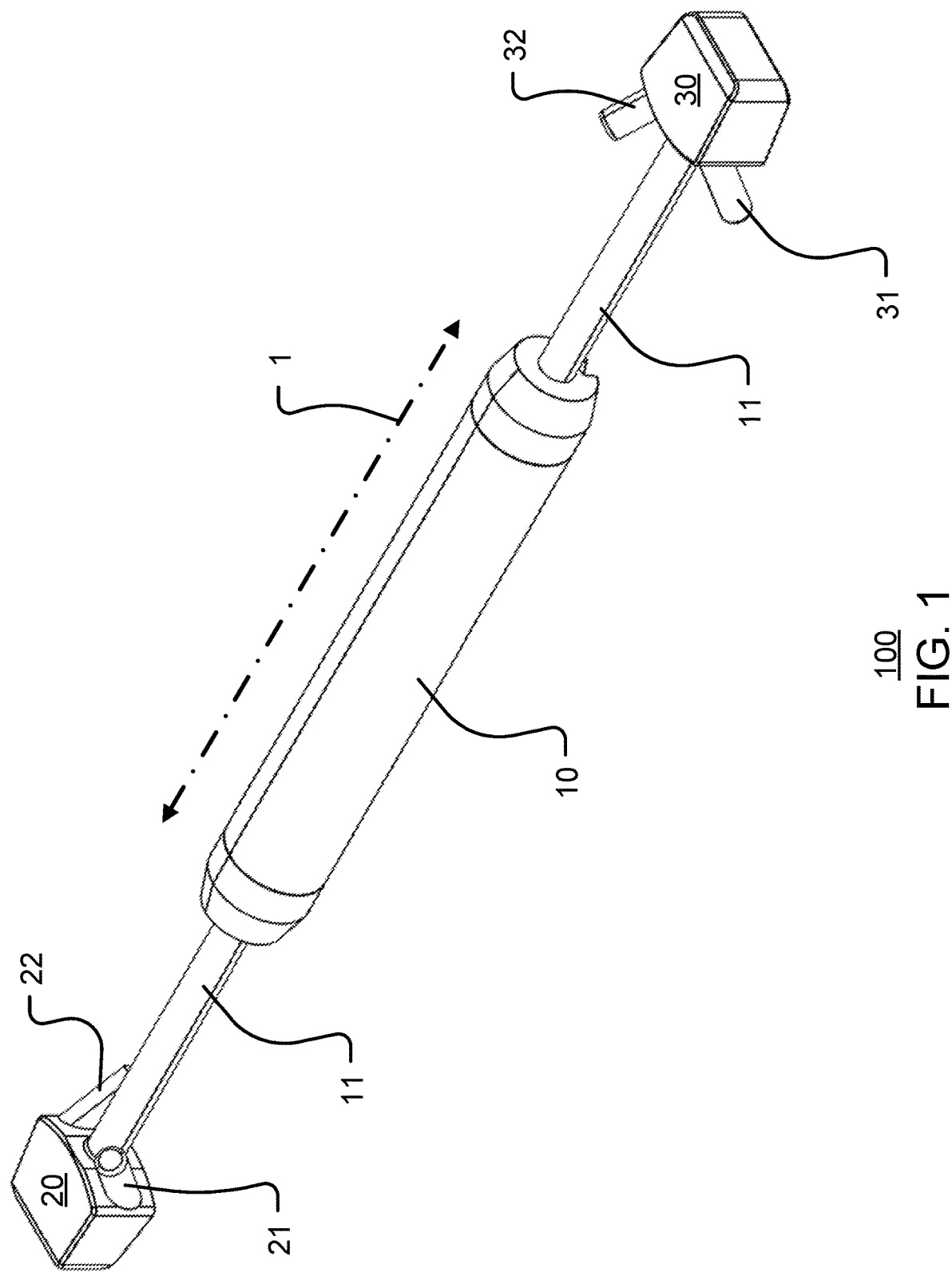
FIG. 1 is a perspective view of an interbody trial tool.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-8B generally, various interbody trial instruments 100 are disclosed. The components of interbody trial instruments 100 can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Figure 2:
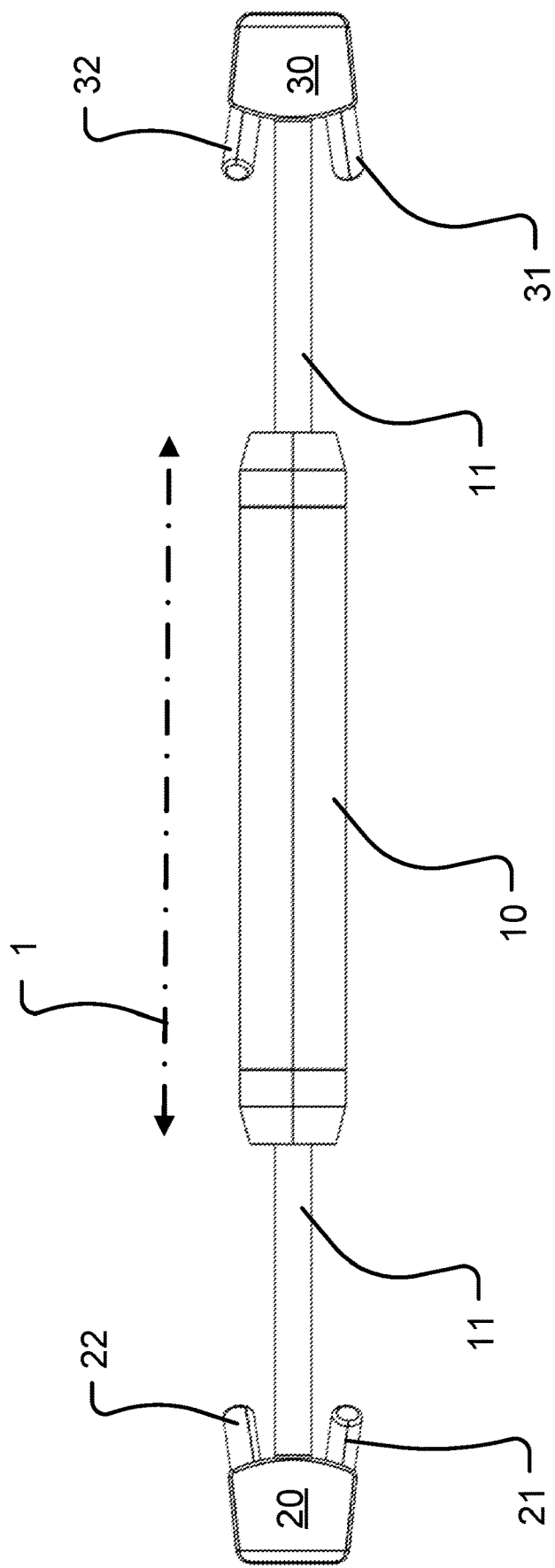
FIG. 2 is a top-down view of the interbody trial tool of FIG. 1.
Figure 3:
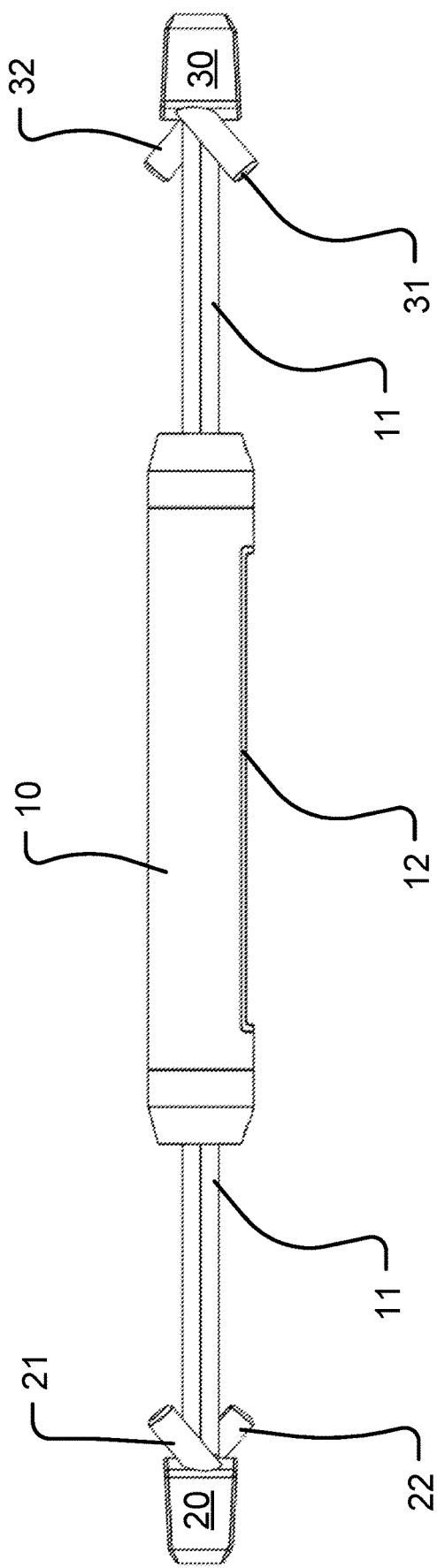
FIG. 3 is a front view of the interbody trial tool of FIG. 1.

FIGS. 1-3 illustrate various views of an interbody trial tool 100. Interbody trial tool 100 may be used by a surgeon for determining an appropriate size, position, and/or orientation of a corresponding interbody implant. For example, a surgeon may first utilize interbody trial tool 100 by positioning either one of the first interbody trial 20 or second interbody trial 30 in between adjacent boney structures to determine what an appropriate size of a corresponding interbody implant may be. The surgeon may utilize the interbody trial tool to determine whether a specific interbody implant having a corresponding size and shape is the appropriate implant for a specific patient. In various embodiments, a surgeon may have two interbody implants (not illustrated) corresponding in size and shape to the first interbody trial 20 and the second interbody trial 30, respectively, and depending on which interbody trial 20, 30 fits best between adjacent boney structures the surgeon may use the best fitting of the two interbody implants for performing a surgical procedure, e.g., a spinal fusion procedure. In addition to helping a surgeon determine an appropriate size and shape of an implant, disclosed interbody trial tool 100 may be used to assist a surgeon in determining that additional preparation of a disc space is warranted. For example, a surgeon may attempt to insert interbody trial tool 100 into a disc space and the surgeon may then recognize that additional cleaning and preparation, such as removal of additional bone portions and/or bone structures such as osteophytes, may be required. In this sense, the interbody trial tool 100 may also assist a surgeon in identifying portions of the boney anatomy that should be removed to clear a path for the body portion of an interbody implant and/or to clear a path for a bone screw extending through the body portion of the interbody implant.

In the example embodiment, interbody trial tool 100 may extend in a longitudinal direction 1 between a first interbody trial 20 and a second interbody trial 30. A medial portion of the interbody trial tool 100 may comprise a handle 10 or gripping portion. In various embodiments, the handle 10 may optionally include a smooth planar surface 12 to facilitate with gripping of a cylindrically shaped handle 10 (as shown in FIG. 3). Additionally, a shaft 11 may extend through the handle 10 and/or be directly coupled or even removably coupled to handle 10. In various embodiments, shaft 11 may support a first interbody trial 20 on a first end of interbody trial tool 100 and a second interbody trial 30 on a second end of the interbody trial tool 100. In other embodiments, interbody trial tool 100 may include a skewed shaft and/or a bayonetted shaft (not illustrated).

As seen best in FIG. 3, interbody trial tool 100 may include two differently sized interbody trials 20, 30. For example, the second interbody trial 30 may be larger and have a greater height, greater width, greater depth, and/or be otherwise alternately shaped than the first interbody trial 20. In various embodiments, at least one of the first interbody trial 20 and second interbody trial 30 may include at least one bone screw protrusion or bone screw indicator for assisting a surgeon with identifying a bone screw trajectory of a corresponding interbody implant. In the example embodiment, the first interbody trial 20 includes a first bone screw indicator 21 and a second bone screw indicator 22 and the second interbody trial 30 includes a first bone screw indicator 31 and a second bone screw indicator 32. In various embodiments, indicators 21, 22, 31, and 32 may take the form of a solid protrusion.

Figure 4:
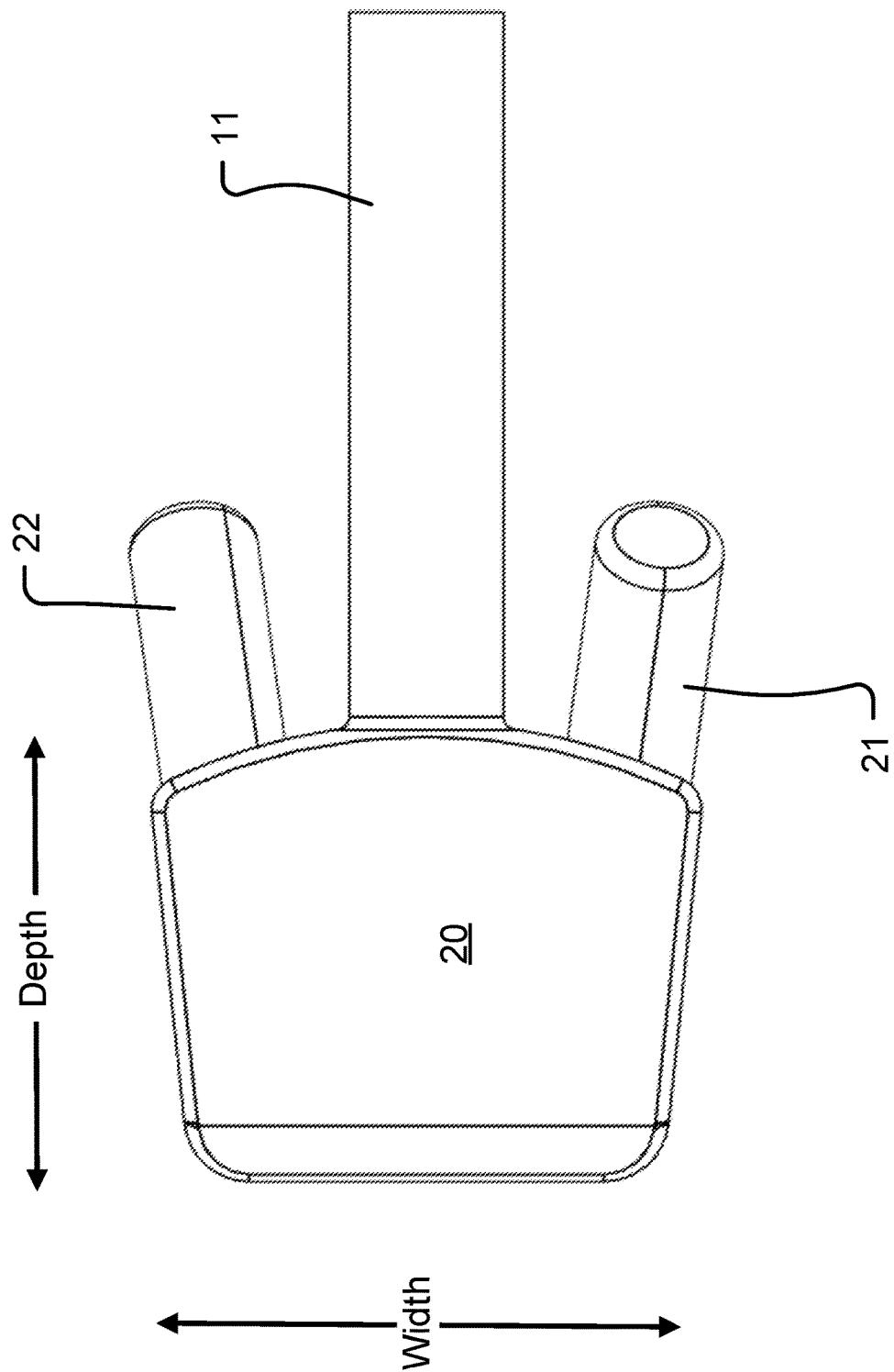
FIG. 4 is a top-down view of a first interbody trial portion.

FIG. 4 is a top-down view of a first interbody trial portion 20 and FIG. 5 is a front view of the first interbody trial portion 20. FIGS. 4-5 illustrate that the first interbody trial portion 20 has a specific geometry including a specific width, a specific depth, and a specific height. With reference back to FIG. 3, the second interbody trial portion 30 may also have a specific geometry including a specific width, a specific depth, and a specific height. In the example embodiment, the second interbody trial portion 30 has a greater height than the first interbody trial portion 20. In various embodiments, the first interbody trial portion 20 may have at least one different dimension and/or contour than the second interbody trial portion 30. Example different dimensions may include a different height, different width, different depth, and or different dimension along an anterior, distal, and/or proximal face. Example different contours may be how the leading edge is chamfered, and/or how an anterior rim may be curved, or an angle of inclination between a superior surface and an inferior surface.

FIG. 6 is a right section view of the first interbody trial portion 20 and FIG. 7 is a front view of the first interbody trial portion 20. In the example embodiment, a first bone screw indicator 21 may be a physical projection that serves as an approximation and/or visual representation and/or guide of a corresponding first bone screw trajectory 211 and second bone screw indicator 22 may be a physical projection that serves as an approximation and/or visual representation and/or guide of a corresponding second bone screw trajectory 222. In the example embodiment, first bone screw indicator 21 may be a physical structure such as a protrusion extending directly from a right section face of first interbody trial portion 20 that visually represents a target bone screw trajectory 211 for a bone screw that may penetrate an inferior vertebrae and/or caudal vertebrae. For example, the first bone screw indicator 21 may be configured to visually represent a first bone screw trajectory 211 for penetrating into an inferior vertebrae and/or caudal vertebrae. In the example embodiment, second bone screw indicator 22 may be a physical structure such as a protrusion extending directly from a right section face of first interbody trial portion 20 that visually represents a target bone screw trajectory 222 for a bone screw that may penetrate a superior vertebrae and/or cranial vertebrae. For example, the second bone screw indicator 22 may be configured to visually represent a second bone screw trajectory 222 for penetrating into a superior vertebrae and/or cranial vertebrae.

In one aspect, the first and second bone screw indicators, 21 and 22 respectively, further provide feedback to a surgeon of proper placement of an implant within a patient by indicating the trajectory that a screw would require or occupy should an implant be placed at the same location as the first interbody trial portion 20. For example, should the trial 20 be positioned such that the bone screw indicators 21, 22 interfere with patient anatomy, the position of the trial 20 should be adjusted to improve access to the contemplated or intended screws. In this manner, the first and second bone screw indicators, 21 and 22 respectively, provide visual feedback as to the contemplated trajectory of screws as well as the access required to insert and drive such screws.

In various embodiments, the first and second bone screw indicators 21, 22 may be a solid protrusion taking the shape of a cylinder, a rectangle, and/or a polygon, for example. In various embodiments, the shape may simulate the envelope of a target path for the largest feature and/or extent a bone screw may take down the target path. In various embodiments, the first and second bone screw indicators 21, 22 may have an aperture therein for serving as a drill guide for drilling pilot holes for a corresponding interbody implant. For example, first bone screw indicator 21 may include a first pilot hole 121 that extends through first interbody trial portion 20 thereby defining first bone screw trajectory 211 and second bone screw indicator 22 may include a second pilot hole 122 that extends through first interbody trial portion 20 thereby defining second bone screw trajectory 222 (see FIG. 6). Although not explicitly illustrated, it shall be understood that the second interbody trial portion 30 may include the same, similar, and/or substantially the same features as first interbody trial portion 20. For example, second interbody trial portion 30 may include similar bone screw protrusions 31, 32 defining similar bone screw trajectories as explained above with respect to first interbody trial portion 20.

Figure 8A:
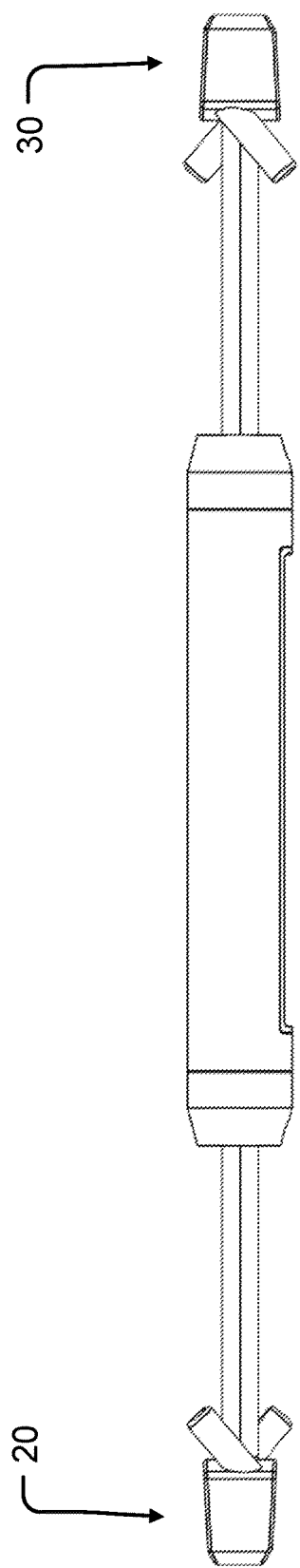
FIG. 8A is a front view of the first interbody trial tool of FIG. 1.
Figure 8B:
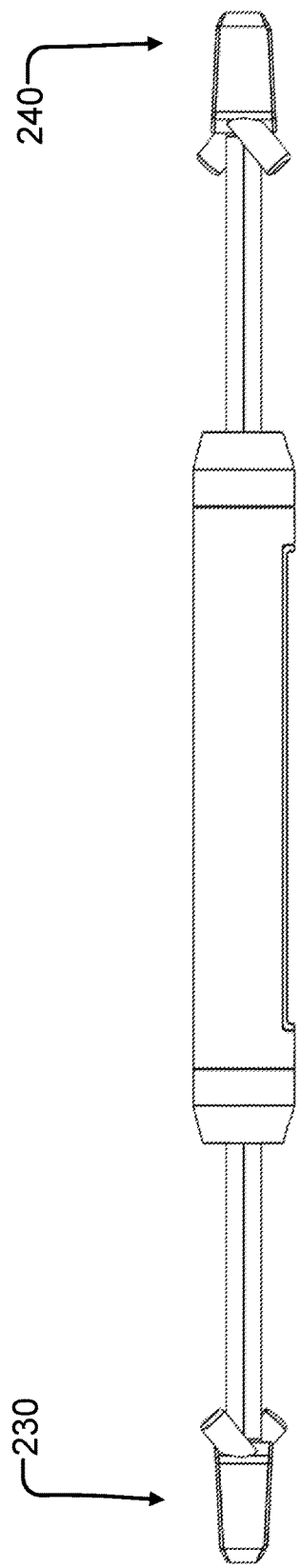
FIG. 8B is a front view of a second interbody trial tool having differently sized interbody trial portions than FIG. 8A.

FIG. 8A is a front view of the first interbody trial tool 100 of FIG. 1 and FIG. 8B is a front view of a second interbody trial tool 200 having differently sized interbody trial portions than FIG. 8A. FIGS. 8A-8B illustrate an interbody trial kit including two interbody trial tools 100, 200 and four differently sized interbody trial portions 20, 30, 230, 240. In the example kit embodiment, second interbody trial 200 includes a first interbody trial portion 230 and a second interbody trial portion 240. In the example embodiment of FIG. 8B, the first interbody trial portion 230 is relatively smaller than the second interbody trial portion. Additionally, the first interbody trial tool 100 includes a first interbody trial portion 20 and a second interbody trial portion 30. In the example embodiment of FIG. 8A, the first interbody trial portion 20 is relatively smaller than the second interbody trial portion 30. Additionally, each of the interbody trial portions 230, 240 of interbody trial tool 200 are smaller than each of the interbody trial portions 20, 30 of interbody trial tool 100. In this way, FIGS. 8A-8B illustrate how a surgeon may utilize a plurality of differently sized interbody trial tools 100, 200 and use any of the plurality of interbody trial portions 20, 30, 230, 240 to ascertain which trial fits best within a specific patient's anatomy and for a particular patient specific surgery. Thereafter, the surgeon may obtain a correspondingly sized interbody implant for performing the surgery with the confidence acquired by conducting trialing of the patient.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. An orthopedic trial instrument, comprising:
a shaft extending from a first end to a second end in a longitudinal direction;
a handle coupled to the shaft; and
a first interbody trial disposed on the first end;
wherein the first interbody trial includes a first bone screw indicator and a second bone screw indicator,
wherein the first bone screw indicator comprises a first cylindrical protrusion extending from a face of the first interbody trial configured to visually represent a corresponding bone screw trajectory for penetrating a superior vertebra, the first cylindrical protrusion being solid and including solid exterior side surfaces and a closed exterior end surface;
wherein the second bone screw indicator comprises a second cylindrical protrusion extending from a face of the first interbody trial configured to visually represent a corresponding bone screw trajectory for penetrating an inferior vertebra, the second bone screw indicator being solid and including solid exterior side surfaces and a closed exterior end surface; and
wherein, with respect to the longitudinal direction, the first cylindrical protrusion extends away from the face of the first interbody trial at an angle and the second cylindrical protrusion extends away from the face of the first interbody trial at an angle.

2. The orthopedic trial instrument of claim 1, further comprising:
a second interbody trial disposed on the second end;
wherein the second interbody trial includes a third bone screw indicator comprising a third cylindrical protrusion extending from a face of the second interbody trial and being configured to visually represent a corresponding bone screw trajectory; and
wherein the third cylindrical protrusion comprises solid exterior side surfaces and a closed exterior end surface.

3. The orthopedic trial instrument of claim 2, wherein:
the second interbody trial includes a fourth bone screw indicator comprising a fourth cylindrical protrusion extending from the face of the second interbody trial and being configured to visually represent a corresponding bone screw trajectory; and
wherein the fourth cylindrical protrusion comprises solid exterior side surfaces and a closed exterior end surface.

4. The orthopedic trial instrument of claim 3, wherein:
the third bone screw indicator is configured to visually represent a corresponding bone screw trajectory for penetrating a superior vertebra and, with respect to the longitudinal direction, the third cylindrical protrusion extends away from the face of the second interbody trial at an angle, and
the fourth bone screw indicator is configured to visually represent a corresponding bone screw trajectory for penetrating an inferior vertebra and, with respect to the longitudinal direction, the fourth cylindrical protrusion extends away from the face of the second interbody trial at an angle.

5. The orthopedic trial instrument of claim 3, wherein:
the first interbody trial comprises a first geometry including a first height, a first width, and a first depth, the first height is defined by a first distance between a first superior surface and a first inferior surface of the first interbody trial;
the second interbody trial comprises a second geometry including a second height, a second width, and a second depth, the second height is defined by a second distance between a second superior surface and a second inferior surface of the second interbody trial;
the first cylindrical protrusion extends to a relative height below the first inferior surface and the second cylindrical protrusion extends to a relative height above the first superior surface,
the third cylindrical protrusion extends to a relative height below the second inferior surface and the fourth cylindrical protrusion extends to a relative height above the second superior surface; and
the first geometry and the second geometry are different.

6. The orthopedic trial instrument of claim 3, wherein:
the first interbody trial comprises a first geometry including a first height, a first width, and a first depth, the first height is defined by a first distance between a first superior surface and a first inferior surface of the first interbody trial;
the second interbody trial comprises a second geometry including a second height, a second width, and a second depth, the second height is defined by a second distance between a second superior surface and a second inferior surface of the second interbody trial;
the first cylindrical protrusion extends to a relative height below the first inferior surface and the second cylindrical protrusion extends to a relative height above the first superior surface,
the third cylindrical protrusion extends to a relative height below the second inferior surface and the fourth cylindrical protrusion extends to a relative height above the second superior surface; and
the first height is greater than the second height.

7. The orthopedic trial instrument of claim 1, wherein a length of the first cylindrical protrusion corresponds to a length of a screw such that the first cylindrical protrusion is indicative of a clearance necessary to affix the screw at the bone screw trajectory.

8. A double-sided orthopedic trial instrument, comprising:
a shaft extending in a longitudinal direction from a first end to a second end;
a handle disposed at a medial position of the shaft;
a first interbody trial disposed on the first end, the first interbody trial including a first cylindrically shaped bone screw protrusion configured to visually represent a corresponding bone screw trajectory for penetrating a superior vertebra and a second cylindrically shaped bone screw protrusion configured to visually represent a corresponding bone screw trajectory for penetrating an inferior vertebra; and
a second interbody trial disposed on the second end, the second interbody trial including a third cylindrically shaped bone screw protrusion configured to visually represent a corresponding bone screw trajectory for penetrating a superior vertebra and a fourth cylindrically shaped bone screw protrusion configured to visually represent a corresponding bone screw trajectory for penetrating an inferior vertebra;
wherein the first cylindrically shaped bone screw protrusion, the second cylindrically shaped bone screw protrusion, the third cylindrically shaped bone screw protrusion, and the fourth cylindrically shaped bone screw protrusion each comprise solid exterior side surfaces and a closed exterior end surface,
wherein a length of the first cylindrically shaped bone screw protrusion, the second cylindrically shaped bone screw protrusion, the third cylindrically shaped bone screw protrusion, and the fourth cylindrically shaped bone screw protrusion each corresponds to a length of a screw and are indicative of a clearance necessary to affix the screw at the bone screw trajectory, and
wherein the first interbody trial and the second interbody trial are differently sized and/or shaped.

9. The orthopedic trial instrument of claim 8, wherein:
the first interbody trial comprises a first geometry including a first height, a first width, and a first depth;
the second interbody trial comprises a second geometry including a second height, a second width, and a second depth; and
the first geometry and the second geometry are different.

10. An orthopedic trialing instrument kit, comprising:
a first double-sided orthopedic trial instrument and a second double-sided orthopedic trial instrument,
the first double-sided orthopedic trial instrument comprises:
a first shaft extending in a first longitudinal direction from a first end to a second end;
a first handle disposed at a medial position of the first shaft;
a first interbody trial disposed on the first end, the first interbody trial including a first cylindrically shaped bone screw protrusion configured to visually represent a corresponding bone screw trajectory for penetrating a superior vertebra and a second cylindrically shaped bone screw protrusion configured to visually represent a corresponding bone screw trajectory for penetrating an inferior vertebra; and
a second interbody trial disposed on the second end, the second interbody trial including a third cylindrically shaped bone screw protrusion configured to visually represent a corresponding bone screw trajectory for penetrating a superior vertebra and a fourth cylindrically shaped bone screw protrusion configured to visually represent a corresponding bone screw trajectory for penetrating an inferior vertebra;
the second double-sided orthopedic trial instrument comprises:
a second shaft extending in a second longitudinal direction from a third end to a fourth end;
a second handle disposed at a medial position of the second shaft;
a third interbody trial disposed on the third end, the third interbody trial including a fifth bone screw protrusion configured to visually represent a corresponding bone screw trajectory for penetrating a superior vertebra and a sixth bone screw protrusion configured to visually represent a corresponding bone screw trajectory for penetrating an inferior vertebra; and
a fourth interbody trial disposed on the fourth end, the fourth interbody trial including a seventh bone screw protrusion configured to visually represent a corresponding bone screw trajectory for penetrating a superior vertebra and an eighth bone screw protrusion configured to visually represent a corresponding bone screw trajectory for penetrating an inferior vertebra;
wherein the first through the eighth cylindrically shaped bone screw protrusions each comprise solid exterior side surfaces and a closed exterior end surface, and
wherein a length of the first through the eighth cylindrically shaped bone screw protrusions each corresponds to a length of a screw such that the first through the eighth cylindrically shaped bone screw protrusions are indicative of a clearance necessary to affix the screw at the bone screw trajectory.

11. The orthopedic trialing instrument kit of claim 10, wherein each of the first interbody trial, second interbody trial, third interbody trial, and fourth interbody trial are differently sized and/or shaped.

12. The orthopedic trialing instrument kit of claim 10, wherein:
the first interbody trial comprises a first geometry including a first height, a first width, and a first depth;
the second interbody trial comprises a second geometry including a second height, a second width, and a second depth; and
the first geometry and the second geometry are different.

* * * * *